US00PP22294P3

(12) United States Plant Patent
Chaparro

(10) Patent No.: US PP22,294 P3
(45) Date of Patent: Dec. 6, 2011

(54) PEACH TREE NAMED 'UFSHARP'

(50) Latin Name: *Prunus persica*
Varietal Denomination: UFSharp

(75) Inventor: Jose X. Chaparro, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/592,576

(22) Filed: Feb. 19, 2010

(65) Prior Publication Data

US 2011/0209257 P1 Aug. 25, 2011

(51) Int. Cl.
*A01H 5/00* (2006.01)

(52) U.S. Cl. ..... Plt./197

(58) Field of Classification Search ..... Plt./197
See application file for complete search history.

(56) References Cited

OTHER PUBLICATIONS

Journal of the American Pomological Society, Apr. 2006, vol. 60, No. 2, pp. 95-96.*
Andersen, et al. (University of Florida Extension publication 'HS765') "Sustainability Assessment of Fruit and Nut Crops in North Florida and North Central Florida,".*

* cited by examiner

*Primary Examiner* — Susan McCormick Ewoldt
(74) *Attorney, Agent, or Firm* — Jondle & Associates, P.C.

(57) ABSTRACT

A new and distinct variety of peach tree, denominated 'UFSharp', has a low winter chilling requirement estimated at 325 chill units (cu). The tree is of medium size, has a moderate vigorous and upright growth habit. It has showy, pink flowers, and leaves with globose glands. Trees of 'UFSharp' are self-fertile and regularly bear heavy annual crops of early, mid-season fruit that are large for its ripening season. Fruit are uniformly firm and yellow with non-melting flesh which are clingstone. Fruit are oval, and uniform with substantially symmetrical shape, and have an attractive 50 to 70% bright red skin. The fruit of 'UFSharp' ripens about 6 days after 'UF2000' peach in late May at Gainesville, Fla.

1 Drawing Sheet

Genus and species: *Prunus persica.*
Variety denomination: 'UFSharp'.

BACKGROUND OF THE NEW VARIETY

The present invention relates to a new and distinct variety of peach [*Prunus persica* (L.) Batsch] tree adapted to a sub-tropical (low chill) winter climate. This new tree, named 'UFSharp', produces highly colored, good eating quality, clingstone and non-melting flesh fruit for fresh market in late May at Gainesville, Fla. Contrast is made to 'UF2000' peach (U.S. Plant Pat. No. 12,019), a standard variety, for reliable description. 'UFSharp' is a promising candidate for commercial success in that it has large, attractive red skin, sweet fruit that ripen evenly.

ORIGIN OF THE VARIETY

'UFSharp' peach tree (genotype) originated in a cultivated area of the fruit breeding program at the University of Florida, located at Gainesville, Fla. where it was tested. The seed parent was 'Fla. 90-50 cn' (unpatented), a melting flesh peach with a high red skin color. The pollen parent was 'Fla. 88-6' (unpatented), a non-melting flesh nectarine. Both of these parent varieties were of complex origin in the University of Florida breeding program. 'UFSharp' was selected in 1997 because it exhibited yellow, non-melting flesh, in a large fruit with a bright red skin. It was designated and tested as 'Fla. 97-52c'. It was asexually propagated by budding onto 'Flordaguard' (unpatented) seedling rootstock (for root-knot nematode control) and determined to have unique tree and fruit characteristics making it worthy for commercial fresh fruit production. There are no known effects of this standard rootstock on this scion cultivar. Asexually propagated plants remained true to the original tree and all characteristics of the tree and the fruit have transmitted for 3 generations.

Plant Breeder's Rights for this variety were applied for in South Africa on Apr. 28, 2010. The peach variety 'UFSharp' has not been made publicly available or sold more than one year prior to the filing date of this application.

SUMMARY OF THE VARIETY

The new and distinct variety of peach tree bears fruit that ripen in late May at Gainesville, and has a moderately low chilling dormancy requirement. 'UFSharp' blooms (showy pink flowers) with 'UF2000' peach in early February at Gainesville, Fla. The estimated chilling requirement is 325 chill units, based on bloom time. 'UFSharp' tree has fruit that are clingstone and of good flavor and eating quality. The trees are vigorous, productive and without alternate bearing. Trees attain in two years, a height of two meters and a spread of one and a half meters at Gainesville, Fla. Terminal growth of up to a half meter annually is common on mature 5-year-old trees with normal pruning to a vase shape.

The first fruit ripen in late May at Gainesville, Fla. or in about 100 to 105 days from full bloom, which is about 6 days after 'UF2000'. The fruit are uniformly large, averaging 180 g when properly thinned to a full crop. Ripe fruit have 50 to70% red skin, there is no red pigment in the flesh at the pit. The flower anthers are light orange to yellow, and leaf glands are globose, common characteristics of many standard peach varieties.

DESCRIPTION OF THE PHOTOGRAPH

The accompanying drawing is a color photograph which shows a typical specimen of the fruit, leaf, and stem of the new variety as nearly true as it is reasonably possible to make in a color illustration of this type. The photograph shows an attractive shape and exterior coloration of 6 specimens of fruit above a ruler in side view, stem end view, a blossom end view, a side view showing the suture and a fruit cut longitudinally to show with and without the pit.

DETAILED BOTANICAL DESCRIPTION

The tree, flowers, and fruit may vary in slight detail due to variations in soil type, cultural practices, and climatic condition. The potential for commercial production of fresh fruit by 'UFSharp' is high, due to its attractive red skin over a bright yellow ground color, large fruit of good flavor, and good firmness with even ripening throughout the fruit. The present botanical description is that of the variety grown on 5-year-old trees on 'Flordaguard' rootstock under the ecological conditions prevailing at Gainesville, Fla. Colors (except those in common terms) are described from "The Pantone Book of Color," published by H. N. Abrams, Inc., N.Y. 1990.

Tree:

*Ploidy.*—Diploid.

*Size.*—Trees are medium stature when trained to an open vase form.

*Vigor.*—Moderately vigorous, and must be summer and winter pruned when grown to a vase shape to keep the tree open to get strong fruiting wood in the lower center. Trees respond typically to irrigation and fertilization. Tree growth of 4 to 6 feet in height and 3 to 5 feet in width occurs the first growing season in the field.

*Density.*—Light to medium in branching habit. Pruning is required to open the tree center to promote sunlight entrance for enhancing fruit color and sugar.

*Form.*—Semi-spreading, but easily pruned to vase shape.

*Hardiness.*—Hardy with respect to typical north central Florida winters.

*Bearer.*—Very productive annually without alternate bearing observed. Trees are self fertile and must be fruit thinned to avoid limb breakage and obtain large fruit size. Yields equivalent of 200 bushels (50 lbs. each) per acre have been obtained on 5-year-old hand thinned trees under a commercial simulated orchard culture at Gainesville. Trees annually set several times the number of fruit for a desired crop load.

*Chilling requirement.*—Estimated endodormancy chilling requirement is 325 chill units based on time of bloom and leafing in relation to standard varieties.

Trunk:

*Size.*—Medium trunk diameter attaining 8 cm diameter at a height of 30 cm at the end of 3 years growth at Gainesville, Fla.

*Texture.*—Medium smooth, but changes to medium shaggy as tree ages.

*Bark color.*—Older bark gray, Chinchilla (Pantone 17-1109).

*Lenticels.*—Moderate number (8 to 14 per 4 square inches of surface area of trunk) and medium (8 to 12 mm length perpendicular to the trunk), grey, Sponge (Pantone 16-1118) with the center being yellowish brown, Medal Bronze (Pantone 17-0942).

Branches:

*Size.*—Strong growth of scaffold branches. Fruiting branches are mostly large diameter (4 to 6 mm) and not overly twiggy, resulting in strong fruiting wood. Thus, the tree growth and structure permits easier and faster winter pruning.

*Texture.*—Relatively smooth, numerous lenticels attaining size found on trunk and old scaffolds. Roughness increases with age.

*Color.*—New wood is light green, Leek Green (Pantone 15-0628); Old wood is more brown, Cameo Brown (Pantone 15-1516).

*Crotch angles.*—Angles are selected at 45 to near 90 degrees in first year of tree training. Natural angles are within the normal range of standard varieties for a semi-spreading tree and similar to those of 'Flordagold'.

Leaves:

*Size.*—Medium; 17 to 19 cm length, including the petiole; 3.2 to 3.8 cm width. Measurements were made on vigorous upright shoots of summer growth.

*Thickness.*—Regular and average for commercial nectarine varieties. Not noticeably unusual.

*Form.*—Lanceolate.

*Apex.*—Acute.

*Margin.*—Serrulate, slightly undulate.

*Base.*—Cuneate.

*Surface.*—Upper, glabrous; Lower, medium large veins that are pinnately netted.

*Color.*—Lower surface is green, Peridot (Pantone 17-0336); Upper surface is slightly darker green, Forest Green (Pantone 17-0230).

*Glands.*—Usually 2, small globose glands mostly on lower leaf blade, but occasionally on petiole. Leaf glands on young leaves are light green, Leek Green (Pantone 15-0628), darkening to Avocado (Pantone 18-0430) on older leaves in mid-summer. Size averages between 1 mm in length and 0.3 mm in length.

*Petiole.*—About 1 cm (0.8 to 1.1 cm) length; 1.3 mm diameter. Light green, Beechnut (Pantone 14-0425) on older leaves of summer. Grooved longitudinally.

*Stipules.*—Medium (equal to most commercial peach varieties), usually 2 per bud, and abscising just before leaf becomes full size in summer growth. Color at full size is green, Leek Green (Pantone 15-0628).

*Arrangement.*—Alternate.

Flower buds:

*Hardiness.*—Hardy with respect to north central Florida winters (16° F. minimum observed).

*Abundance.*—Very high due to shorter than average internode length. Most buds set fruit in absence of spring frosts and show little evidence of bud drop.

*Size.*—Medium, average 3.5 mm length in mid winter.

*Form.*—Plump, conic and free.

*Surface.*—Pubescent scales.

*Color.*—Brown, Stucco (Pantone 16-1412) in late summer.

Flowers:

*Blossom period.*—Blooms 2 to 3 days before 'UF2000' peach — average 50% bloom February 10 to 15 most years at Gainesville, Fla., but occurring over a 7-10 day period. Time and length of bloom are dependent on ambient temperature.

*Aroma.*—Slight and pleasant.

*Flower density.*—Abundant, varying from 1 to 3 per node, but usually 2.

*Type.*—Showy, location and seasonally variable within the range of commercial showy varieties.

*Average flower diameter.*—3.0 cm.

*Average petal size.*—Length, 13 mm; width, 10.0 mm.

*Texture.*—Smooth.

*Margins.*—Undulate and smooth.

*Color.*—Orchid Pink (Pantone 13-2010) at flower opening, and within the pink range of standard varieties.

Flower parts: Stamens and pistil size, shape and color are within the range of standard commercial varieties. There are 5 sepals and petals. Sepals average 4 mm length and 4 mm wide at attachment to calyx cup and rounded at the distal end. Sepals are green, Grasshopper (Pantone 18-0332) on the interior and red, Cardinal (Pantone 18-1643) on the exterior with a smooth pubescent margin. Sepals are pubescent and petals are glabrous. Pistils are usually 1 per flower and straight (without curls or curves) just prior to flower opening. Pistil length (from tip of stigma to base of ovary) averages 14 mm. Pistils are light green, Pale Star (Pantone 12-0626). Flower pedicel is 1 to 2 mm length.

*Calyx cup.*—Medium small in the size range of commercial varieties. Calyx cup diameter is 5 mm at the time of flower opening. Calyx exterior is red, Cardinal (Pantone 18-1643) and interior is orange, Persimmon Orange (Pantone 16-1356).

*Stamen.*—Anthers are orange, Flamingo (Pantone 16-1450), at flower opening, fading to yellow, Banana (Pantone13-0947), before pollen sheds. Number of anthers varies from 27 to 36, length is 7-9 mm. Filaments are light green, Pale Star (Pantone 12-0626).

*Pollen.*—Abundant and bright yellow, Snapdragon (Pantone 13-0840), common to many peach varieties.

*Fertility.*—Fully self fertile, and no cross pollination is required. Fruit set is abundant.

Fruit:

*Maturity when described.*—Tree ripe, May 20, 2004 at Gainesville, Fla.

*Date of picking.*—First, May 20, 2004; Last, — May 28, 2004 at Gainesville, Fla.

*Size.*—Uniform, medium large (large size for early mid-season maturity at 150 to 180 g). Varies with fruit number per tree, soil type, climatic conditions and cultural practices.

*Average equatorial diameter.*—59 mm.

*Average polar length* (*stem to distal end*).—65 mm.

*Pedicel size and color.*—Length is approximately 7 mm; Width is approximately 3 mm. Color is green, Mellow Green (Pantone 12-0426.

*Longitudinal section form.*—Strongly oval.

*Transverse section through diameter.*—Round.

*Suture.*—Shallow and inconspicuous except for a crease on the stem end of the fruit.

*Ventral surface.*—Usually rounded.

*Base.*—Slightly cordate.

*Apex.*—Usually rounded to slightly obtuse.

*Crater at stem attachment.*—Flaring circular with slight suture crease at the stem end. Depth is 6 to 9 mm; breadth is 18 mm at top and 4 mm at pedicel attachment.

Skin:

*Thickness.*—Medium in comparison to commercial peach varieties.

*Texture.*—Medium in comparison to commercial peach varieties.

*Tenacity.*—Tenacious to flesh.

*Color.*—Bright red, Grenadine (Pantone 17-1558), over 50 to 70% of skin. Ground color is rich yellow, Sunset Gold (Pantone 13-0940). Fruit exposed to sunlight have a higher degree of enhanced red skin.

*Tendency to crack.*—None observed.

*Taste.*—No astringency observed.

*Epidermis.*—Pubescent, but slightly shorter than 'UF2000'.

Flesh:

*Ripens.*—Evenly within each fruit.

*Texture.*—Firm, juicy, melting when fully ripe.

*Fibers.*—Very fine, small, tender, and abundant.

*Aroma.*—Moderate and in the middle range of commercial peach varieties.

*Eating quality.*—Good, moderately sweet, slightly acid. Soluble solids vary from 12 to 14 brix and titratable acid was 0.46 at 2.4 kg penetrometer firmness.

*Juice.*—Abundant.

*Color.*—Bright yellow, Spectra Yellow (Pantone 14-0957), with no red in the flesh near the fruit tip, especially on stressed trees under dry, hot conditions. There is no red at the pit.

*Browning by oxidation.*—Not detectable on tree ripe fruit beginning to soften.

*Amygdalin.*—Undetected.

Stone:

*Type.*—Clingstone.

*Size.*—Medium small: average length is 30 mm; average width is 21 mm; average thickness is 16 mm; average wall thickness is 5-6 mm.

*Color.*—Light Brown, Topaz (Pantone 16-1150) when flesh is freshly cut.

*Form.*—Oblong.

*Base.*—Straight.

*Apex.*—Acute.

*Sides.*—Near equal.

*Surface.*—Irregularly furrowed toward the ventral edge, pitted from base to apex.

*Ridges.*—Jagged toward the base.

*Tendency to split.*—None observed.

Seed:

*Bitter* (*amygdalin is abundant*) *kernel.*—Viable if stratified upon removal from fruit at harvest, and without drying. Kernel is brown, Sunflower (Pantone 16-1054) when first removed from ripe fruit. Side is 15 mm length, 8 mm wide and 4 mm thick. The seed has an acute tip with an obtuse base and an overall ovate shape.

Use: Fresh; dessert.

Resistance to disease: High resistance to bacterial spot incited by Xanthomonas campestris pv. pruni (Pers.). Resistance to other fruit and tree diseases are within the range for commercial peach cultivars in Florida. No unusual resistance or susceptibility to insects and diseases noted.

Keeping quality: Excellent after 10 days at 2° C. and with minimal bruises or scarring appearing on skin.

Shipping quality: Degree of firmness at harvest and firmness retained in refrigeration for 10 days at 2° C., with no internal breakdown of flesh or appreciable loss of eating quality, indicates fruit should be highly acceptable for shipping.

COMPARISON WITH PARENTAL AND COMMERCIAL VARIETIES

The new peach variety 'UFSharp' differs from its seed parent, 'Fla. 90-50 cn' (unpatented) in that it is a non-melting flesh peach, while the seed parent is a melting flesh peach. 'UFSharp' differs from its pollen parent, 'Fla. 88-6' (unpatented) in that while 'UFSharp' is a peach, 'Fla. 88-6' is a nectarine.

The new peach variety 'UFSharp' can be compared to commercial varieties. The fruit of 'UFSharp' ripens about six days after the fruit of commercial peach variety 'UF2000' (U.S. Plant Pat. No. 12,019), and about 21 to 24 days after the commercial peach variety 'UFGold' (U.S. Plant Pat. No. 10,315). Additionally, 'UFSharp' has bright red colored fruit skin (Grenadine; Pantone 17-1558), with a rich yellow ground color (Sunset Gold; Pantone 13-0940). In contrast, the fruit skin of commercial variety 'UF2000' is Paprika (Pantone 17-1553) with a ground color of Sun Orange (Pantone 16-1257).

We claim:

1. A new and distinct variety of peach tree named 'UFSharp' as shown and described herein.

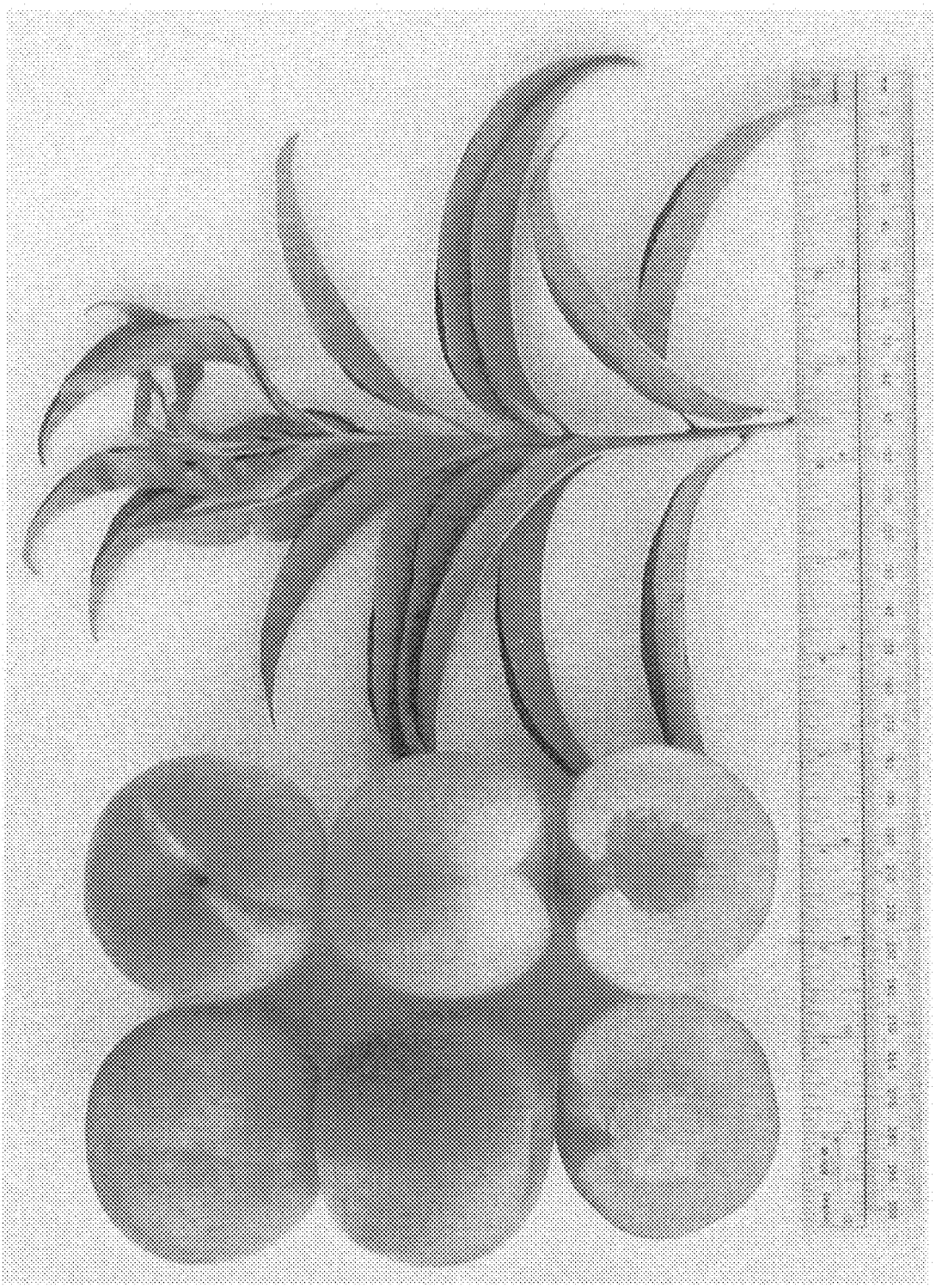

* * * * *